(12) United States Patent
Kaplan et al.

(10) Patent No.: US 6,712,831 B1
(45) Date of Patent: Mar. 30, 2004

(54) METHODS AND APPARATUS FOR FORMING ANASTOMOTIC SITES

(76) Inventors: Aaron V. Kaplan, 851 Carnation Ct., Los Altos, CA (US) 94024; Jordan T. Bajor, 1183 Lincoln Ave., Palo Alto, CA (US) 94301

( * ) Notice: Subject to any disclaimer, the term of this patent is extended or adjusted under 35 U.S.C. 154(b) by 148 days.

(21) Appl. No.: 09/595,746

(22) Filed: Jun. 16, 2000

(51) Int. Cl.[7] .............................................. A61B 17/08
(52) U.S. Cl. .................................................... 606/153
(58) Field of Search ........................... 606/1, 108, 159, 606/153, 154, 170, 184, 185, 194, 195, 198; 604/96.01

(56) References Cited

U.S. PATENT DOCUMENTS

| | | | |
|---|---|---|---|
| 4,744,364 A | 5/1988 | Kensey | |
| 4,794,928 A | 1/1989 | Kletschka | |
| 5,192,301 A | 3/1993 | Kamiya et al. | |
| 5,222,974 A | 6/1993 | Kensey et al. | |
| 5,330,446 A | 7/1994 | Weldon et al. | |
| 5,342,393 A | 8/1994 | Stack | |
| 5,350,399 A | 9/1994 | Erlebacher et al. | |
| 5,383,896 A | 1/1995 | Gershony et al. | |
| 5,496,332 A | 3/1996 | Sierra et al. | |
| 5,593,422 A | 1/1997 | Muijs Van de Moer et al. | |
| 5,630,833 A | 5/1997 | Katsaros et al. | |
| 5,676,670 A * | 10/1997 | Kim | 606/108 |
| 5,690,674 A | 11/1997 | Diaz | |
| 5,700,277 A | 12/1997 | Nash et al. | |
| 5,766,220 A | 6/1998 | Moenning | |
| 5,782,860 A | 7/1998 | Epstein et al. | |
| 5,922,009 A | 7/1999 | Epstien et al. | |
| 5,925,054 A * | 7/1999 | Taylor et al. | 606/108 |
| 5,944,730 A | 8/1999 | Nobles et al. | |
| 5,951,589 A | 9/1999 | Epstein et al. | |
| 6,165,196 A * | 1/2000 | Stark et al. | 606/194 |
| 6,068,637 A * | 5/2000 | Popov et al. | 606/159 |
| 6,143,015 A * | 11/2000 | Nobles | 606/194 |
| 6,395,015 B1 * | 5/2002 | Borst et al. | 606/153 |

FOREIGN PATENT DOCUMENTS

| | | |
|---|---|---|
| EP | 894475 | 3/1999 |
| WO | WO 95/17127 | 6/1995 |
| WO | WO 97/47261 | 11/1997 |

\* cited by examiner

*Primary Examiner*—George R. Evanisko
(74) *Attorney, Agent, or Firm*—Townsend and Townsend and Crew, LLP

(57) ABSTRACT

Apparatus and methods are provided for forming a working space on the interior wall of a blood vessel, such as the aorta. The working space is isolated from blood flow and permits creation of an anastomotic hole and subsequent suturing of the hole to form an end-to-side anastomosis, even while the heart is beating. The apparatus comprises tools including inflatable barriers, such as cup-shaped balloons, which engage the inner wall of the blood vessel with minimum trauma and maximum sealing. In a first embodiment, the inflatable barrier is introduced through a penetration at the site of the anastomotic attachment. In a second embodiment, the inflatable barrier is introduced through a second penetration axially spaced-apart from the site of the anastomotic attachment.

22 Claims, 13 Drawing Sheets

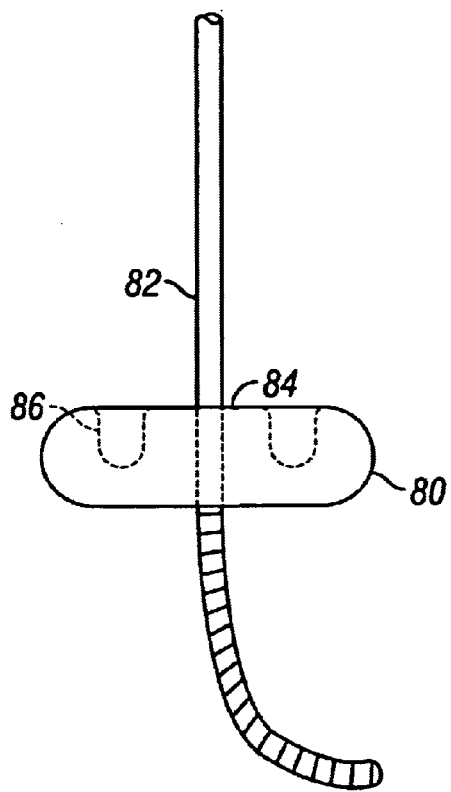 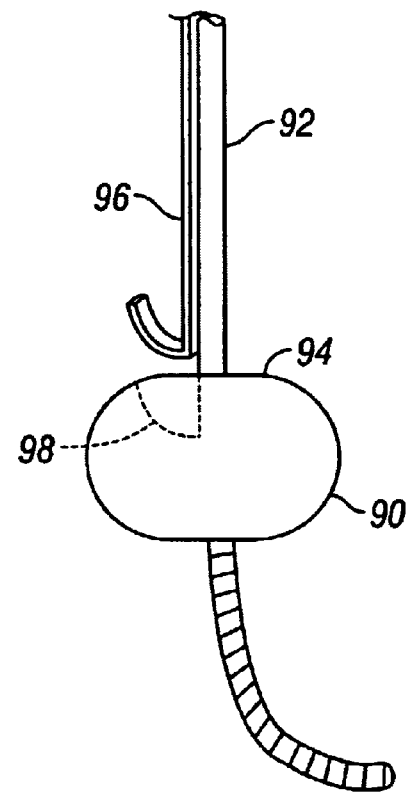
FIG. 3A  FIG. 3B

METHODS AND APPARATUS FOR FORMING ANASTOMOTIC SITES

BACKGROUND OF THE INVENTION

1. Field of the Invention

The present relates generally to medical apparatus and methods. More particularly, the present invention relates to methods and apparatus for creating isolated working spaces within the lumen or a blood vessel to facilitate forming end-to-side anastomoses.

Coronary artery bypass graft (CABG) surgery remains one of the most common treatment for coronary artery disease in the United States and other developed countries. Vein grafts, typically harvested from the patient's legs are connected to the aorta and then to the coronary arteries beyond diseased regions. This procedure is typically performed with the patient's heart stopped after initiation of cardiopulmonary bypass. Cardiopulmonary bypass and stopping the heart has been associated with stroke as well as heart muscle damage. To reduce these risks, surgeons have developed techniques to perform CABG while the heart is still beating avoiding cardiopulmonary bypass.

CABG using beating heart technique is performed in the following manner. After obtaining the appropriate level of anesthesia, the surgeon makes an incision over the sternum after which the sternum is divided. The pericardial sac is opened and the patient's aorta and heart are identified and examined. Simultaneously, saphenous veins are harvested from the patient's legs. The surgeon clamps the aorta with a side biting clamp, partially occluding the aorta. A small incision in the aorta is made after which hole punch device is used to make an appropriate size hole, typically 4–6 mm in diameter. The saphenous vein is then sutured onto the aorta. Similarly, the site on the coronary artery where the distal anastomosis will be placed is identified after which an incision is made and the vein sutured.

Clamping the aorta using the side biting technique as well as using cross clamp technique as used during cardiopulmonary bypass, is associated with trauma to the aorta as well as releasing plaque in to the circulation possibly causing a stroke.

In order to at least partially overcome these difficulties, U.S. Pat. No. 5,944,730 proposes to use a device which can create a working space on the interior surface of a blood vessel wall without interrupting the flow of blood through the blood vessel, such as the aorta. The device comprises an inverted cone at the end of a shaft, where the cone can be deployed in the manner of an umbrella. The peripheral lip of the cone is then drawn proximally against the interior wall to isolate the working space from blood flow. The device is useful in stopped heart procedures as well as in beating heart procedures.

Although promising, the device of U.S. Pat. No. 5,944,730, itself suffers from certain limitations. The inverted cone is a rather rigid structure which may have difficulty mating and sealing against the interior surface of the aorta or the blood vessel. Moreover, the relatively rigid nature of the cone can itself disrupt and dislodge plaque from the interior of the aorta, presenting an immediate risk of stroke and peripheral vascular damage since circulation has not been stopped. Additionally, the mechanical structure of the device will require a relatively large profile, making removal of the device after an end-to-side anastomosis has been formed somewhat difficult. In short, the device of U.S. Pat. No. 5,944,730, is complex, cumbersome, and difficult to deploy.

For these reasons, it would be desirable to provide improved and alternative methods and devices for forming working spaces within the aorta and other blood vessels without the need to stop blood flow through the blood vessel. In particular, it would be desirable to create isolated regions or "working spaces" on the aorta wall which are suitable for preparing an anastomotic hole which can subsequently be sutured or otherwise attached to a saphenous vein or other graft. The devices used to form such working spaces should be capable of forming tight seals with the inner wall of the aorta with minimum trauma and risk of emboli release. The devices should have a low profile to facilitate both introduction to the aorta or the blood vessel as well as withdrawal from the blood vessel lumen after the anastomosis has been formed. At least some of these objectives will be met by the inventions described hereinafter.

2. Description of the Background Art

U.S. Pat. No. 5,944,730, describes a device having an inverted shell that is mechanically deployed within a blood vessel lumen to create a working space for performing an end-to-side anastomosis. The device has a relatively large profile and requires an incision for initial placement in the blood vessel. The deployable shell would not be expected for form an optimum seal with the interior blood vessel wall after deployment.

Other devices for locating and/or creating isolated regions within blood vessels for anastomotic attachments are described in EP 894 475 and PCT publications WO 97/47261 and WO 95/17127.

Devices for sealing punctures in blood vessel walls, atrial septums, and the like, are described in U.S. Pat. Nos. 4,744,364; 4,794,928; 5,192,301; 5,222,974; 5,330,446; 5,342,393; 5,350,399; 5,383,896; 5,496,332; 5,593,422; 5,630,833; 5,690,674; 5,700,277; 5,766,220; 5,782,860; 5,922,009; and 5,951,589.

SUMMARY OF THE INVENTION

The present invention provides methods, apparatus, and kits for forming an anastomotic site in the wall of a blood vessel or other body lumen, usually an artery, and more usually the aorta. The anastomotic site will be useful for connection of a graft vessel, typically a portion of the patient's own saphenous vein which is harvested earlier in the procedure. Other conduits which may be harvested include the brachiocephalic vein as well as the radial and internal mammary arteries. In addition to the use of harvested veins, grafts formed from ePTFE, dacron, and the like, may also find use under certain circumstances. Other body lumens where anastomotic sites may be formed using the present invention include the intestines, both small and large.

The working surface formed by the methods of the present invention will be a small volume within the lumen of the blood vessel which is isolated from blood flow which would otherwise pass through that space. The working space will usually be circular or annular in the region where it interfaces with the inner wall of the blood vessel, usually having a diameter in the range from 3 mm to 10 mm, more usually from 4 mm to 6 mm. As described in more detail below, the working space will be defined by an inflatable barrier which typically has a hemispherical or ovoid geometry. The volume of the working space will generally be from 7 $mm^3$ to 250 $mm^3$, usually from 20 $mm^3$ to 50 $mm^3$. Once formed on the inner wall of the blood vessel, the working space will be available for any desired purpose. Usually, the space will be used initially to permit cutting or punching of an anastomotic hole through the blood vessel wall, where the hole will open wholly into the working space. Additionally, after the anastomotic hole is formed, the working space will usually be used to accommodate the needles used to suture a distal end of the graft vessel to the anastomotic hole in the blood vessel wall.

Of particular interest to the present invention, the working space will be formed by an inflatable barrier which has a recessible surface which is positioned or engaged against the inner surface of the blood vessel wall. The inflatable barrier will have a very low profile prior to inflation, typically having an outer diameter below 2 mm, preferably below 1.5 mm. Additionally, after deflation, the inflatable barrier will again have a low profile to facilitate withdrawal from the blood vessel through which the anastomosis is being formed. The recessible surface may be performed as part of the geometry of the inflatable barrier. That is, the recession may form as the barrier is inflated. In such cases, the recession may be concave, annular, or have some other complex shape which accommodates a particular purpose. Alternatively, the recessible surface may comprise an elastic or otherwise deformable region of the inflatable barrier where the region can be deformed by a separate tool after inflation, such as by using a separate needle shield tool as described below.

In a first aspect, methods according to the present invention will form an anastomotic site in a blood vessel having a wall with an outer surface, an inner surface, and an interior lumen. The inflatable barrier is positioned so that its concave surface lies against the inner surface of the blood vessel wall. The balloon will preferably be made from an elastomeric or other conformable material so that it can conform to and seal tightly against the inner surface of the wall. After the barrier is inflated, the isolated working space is created interior to the inner surface of the blood vessel wall. A hole may then be cut through the wall into the working space to create the anastomotic site, while the site remains isolated from flowing blood by the inflated barrier. In a first embodiment of the method, the barrier is positioned while in a deflated condition through a penetration in the blood vessel wall into the lumen. The barrier may be introduced directly through a separately formed incision in the blood vessel wall, or may be positioned using an access needle in a Seldinger approach. In a Seldinger approach, the inflatable barrier is positioned within the Seldinger needle, and the needle withdrawn proximally over the barrier after the barrier has been properly positioned. After positioning, the barrier is inflated, and the concave surface of the barrier drawn backwardly against the inner surface of the blood vessel wall to locate the working space over the initial penetration. Optionally, after the Seldinger needle is removed, it may be exchanged for a removal sheath which remains in place over the catheter to facilitate removal of the inflatable barrier at the end of the procedure. In cases where the catheter is introduced through a Seldinger needle and/or a removal sheath is placed over the catheter, it will be necessary that the catheter have a removal inflation hub at its distal end to permit introduction and withdrawal of the devices thereover.

Once the working space is established, the anastomotic hole may be formed, conveniently using a conventional cutting die. Optionally, the cutting die can be modified in some way to accommodate presence of the catheter extending outwardly through the anastomotic hole. The catheter must, of course, remain in place so that the physician can continue to pull proximally on the catheter in order to maintain the desired sealing and isolation of the working space. Thus, the anastomotic hole will have to be formed in such a way as to avoid interference from the catheter. One way of achieving such non-interference is to provide a channel in the side of an otherwise conventional anastomotic hole punch in order to accommodate the presence of the catheter.

Once the anastomotic hole is formed, the methods of the present invention will usually further comprise attaching a distal end of a graft vessel to the anastomotic site, typically using conventional manual suturing. After the anastomotic connection is substantially complete, the catheter and deflated inflatable barrier may be removed from between the graft and the aorta, and the suture attachment tightened and completed quickly after the site is again exposed to flowing blood.

In an alternative protocol according to the present invention, the inflatable barrier may be positioned through a first penetration in the blood vessel wall and into the blood vessel lumen. The barrier is then advanced axially through the blood vessel lumen away from the first penetration. Usually, the second penetration is formed at the location of the working space and a tether passed through the second penetration. The tether is attached to the inflatable barrier through the second penetration, and thus pulling on the tether will draw the inflatable barrier against the inner surface of the blood vessel at the working site. The balloon is inflated and the barrier is further drawn against the arterial wall at the working site to the desired tension by pulling on the tether. Presence of the tether, which may be a single filament or length of suture, is advantageous in that it presents little interference to formation of the anastomotic hole and subsequent suturing of the graft to the hole. Moreover, both the inflatable barrier and the tether may be withdrawn proximally so that they pass outwardly through the second penetration, thus allowing the anastomosis to be substantially completed before deflation of the inflatable barrier. The tether which remains within the newly anastomosed site can be readily withdrawn inward without disturbing the anastomosis.

In a particular embodiment of the alternative protocol, the inflatable barrier is deployed by first passing a curved needle in through the first penetration and then outward through the second penetration in the blood vessel wall. The needle is attached to the tether which is used to draw and position the inflatable barrier at the target anastomotic site. Usually, the inflatable barrier will be mounted at the end of a shaft, and the shaft will be curved to facilitate locating the concave surface of the barrier back against the inner wall of the blood vessel.

In the second protocol, after the inflatable barrier has been positioned, the anastomotic hole may be formed by introducing a cutting die over or adjacent to the tether. If the cutting die is advanced adjacent to the tether, a channel may optionally be formed in the cutting die to accommodate the tether as the cutting die is advanced.

As with the first protocol, after the anastomotic hole is formed, the distal end of the graft vessel will be sutured or otherwise attached to the anastomotic hole while the tether remains in place between the newly placed graft vessel in the hole. As described above, however, the tether will then be withdrawn outwardly through the first penetration (not the anastomotic hole) in order to lessen interference with the anastomosis which has just been created.

As the isolation barrier will usually be in place as the graft vessel is sutured (anastomosed) to the aorta or the blood vessel, it is desirable that the inner surface of the inflatable barrier be protected. This is particularly in the case when the inflatable barrier is an elastomeric balloon formed from conventional materials, such as silicone rubber, latex, or the like. In a first instance, the balloon may be protected by forming a penetration-resistant barrier over at least a portion of the concave surface. In this way, after the barrier is deployed, accidental needle penetration through the barrier will be inhibited. In a second instance, a separate needle penetration guard may be introduced through the penetration and/or anastomotic hole prior to either cutting or suturing. For example, the guard may comprise a shield formed at the end of a separate shaft so that the shield can be positioned adjacent to the barrier when needed to protect the barrier.

In a further optional aspect of the methods of the present invention, concave surface of the barrier will be drawn against the inner surface of the blood vessel wall by pulling outwardly on the catheter body. In such instances, the catheter may be constructed to yield in response to axial tension, i.e., to stretch as the inflatable shield is drawn against the inner surface of the blood vessel wall. Such stretching will modulate the force applied against the inner surface of the blood vessel wall. This will allow the inflatable barrier to be drawn against the arterial wall at the working site with the proper tension, thus reducing vessel trauma. In a further optional aspect, after the catheter has been positioned, the anastomotic hole formed and hemostasis established, such stretchable tool shafts can be held in place by a mechanical apparatus usually fixed to the sternal retractor.

Apparatus according to the present invention for isolating a working space in a blood vessel having a wall with an outer surface, an inner surface, and an interior lumen comprise an inflatable barrier and means for introducing and deploying the inflatable barrier through penetration in the blood vessel wall. The inflatable barrier will have a recessible surface, as previously described, which is adapted to conform to and seal against the inner surface of the blood vessel wall to define the desired working space.

The means for introducing can take a variety of forms, but will usually comprise a shaft having a proximal end, a distal end, and an inflation lumen therethrough. The inflatable barrier is attached at or near the distal end of the shaft, and the recessible surface of the barrier may be disposed in either a proximal direction (so that the barrier may be deployed by pulling backwardly on the shaft to engage the surface against the blood vessel wall) or distally (so that the recessible surface may be deployed by advancing the shaft forwardly). The shaft itself may be straight, which is particularly useful in those embodiments where the barriers be deployed at a proximal direction. In some instances, at least a portion of the straight shafts will be formed so that they yield to axial tension so that the shaft can stretch as it is being deployed. Alternatively, when the inflatable barrier is to be deployed with the recessible surface disposed distally, the shaft will usually be curved so that the barrier can be engaged against the inner wall of the blood vessel by pushing the shaft forwardly and upwardly against the desired location, where the shaft is introduced through a penetration spaced-apart from the desired location. Optionally, in at least the straight shaft embodiments, the apparatus may further comprise a guidewire extending distally from the distal tip of the shaft. The guidewire is advantageous because it allows for the advancement of the catheter in a blind fashion with minimal trauma to the luminal surface of the arterial wall.

As an alternative or an addition to the shafts described above, the introducing means may comprise a tether attached to the concave surface of the barrier. In such cases, the tether will be adapted to be passed through a penetration in the blood vessel wall to permit positioning of the inflatable barrier by drawing outwardly on the tether. While the tether itself may be all that is needed to deploy the barrier, a separate curved shaft will usually be joined to the inflatable barrier in addition to the tether, as described in the specific embodiments below.

Preferably, the introducing means comprising a tether will further comprise a curved needle attached to a distal end of the tether. In this way, the curved needle can be introduced to the blood vessel to form a first penetration and an axially spaced-apart second penetration. The tether can then be drawn through both penetrations in order, and the tether then used to draw the concave surface of the inflatable barrier against the desired anastomotic site which is located adjacent to the second penetration. The first penetration will then be available to accommodate a positioning and an inflation shaft, as described above in connection with the methods of the present invention.

The inflatable barriers of the apparatus of the present invention will typically comprise balloons, more typically elastomeric balloons which present minimum risk of trauma to the blood vessel and which can readily conform to the interior surface of the aorta or other blood vessel. The inflatable balloons will have a "recessible surface" which provides the isolated working space. Most simply, the barrier can have a cup-shaped geometry with the interior of the cup defining the working space. Alternatively, the geometry or contour of the inflated balloon may be complex and present a trough or channel at the margins of the anastomotic hole to provide a working space for the anastomotic or other subsequent procedure. In another embodiment the balloon may have a flat or even convex configuration where the working space is created by compressing the balloon with the penetration shield or other rigid tool. The shape and volume of the working space defined by the cup is generally as described above in connection with the methods of the present invention. The inflatable elastomeric balloon will optionally comprise a needle penetration shield formed over at least a portion of the concave surface. The shield will typically be formed from a penetration-resistant polymer, such as polyimide. Alternatively, if a separate needle penetration barrier is to be used, the elastomeric balloon need not have a separate penetration-resistant layer. It will be appreciated that elimination of the penetration-resistant barrier may be desirable in order to produce the profile of the balloon in its non-inflated condition. Alternatively, inclusion of the penetration-resistant barrier is desirable in order to reduce the risk of accidentally damaging the balloon.

The present invention further comprises systems and kits. A system according to the present invention comprises any of the straight shaft isolation barriers in combination with a sheath. The sheath may be useful to facilitate removal, as described above. Alternatively, in the case of shafts which can stretch or otherwise deform, the sheath may be useful to facilitate introduction of the shaft (as well as possible removal of the shaft).

Additional kits according to the present invention comprise the apparatus described above in combination with a tool comprising a shaft and a needle penetration shield. The tool may thus be separately deployed to protect the balloons of the apparatus from damage during anastomosis procedures.

Kits according to the present invention will comprise an inflatable barrier, generally as described above, in combination with instructions for use setting forth any of the methods described above. The kits may further comprise the removal sheath, introduction sheath, penetration shield tool, anastomotic hole punch, inflation syringe, scalpel, or other system components which may be used for performing the methods of the present invention. Usually, the kit will comprise conventional medical device packaging, such as a box, tube, tray, pouch, or the like, and the instructions for use may be printed on a separate instruction sheet and/or on the packaging itself. The system components will be maintained within the packaging, typically being maintained in a sterile condition.

BRIEF DESCRIPTION OF THE DRAWINGS

FIG. 3A illustrates an inflatable barrier having an alternative configuration.

FIG. 3B illustrates an inflatable barrier having a recessible surface which is recessed by a rigid tool.

DESCRIPTION OF THE SPECIFIC EMBODIMENTS

Figure 1:
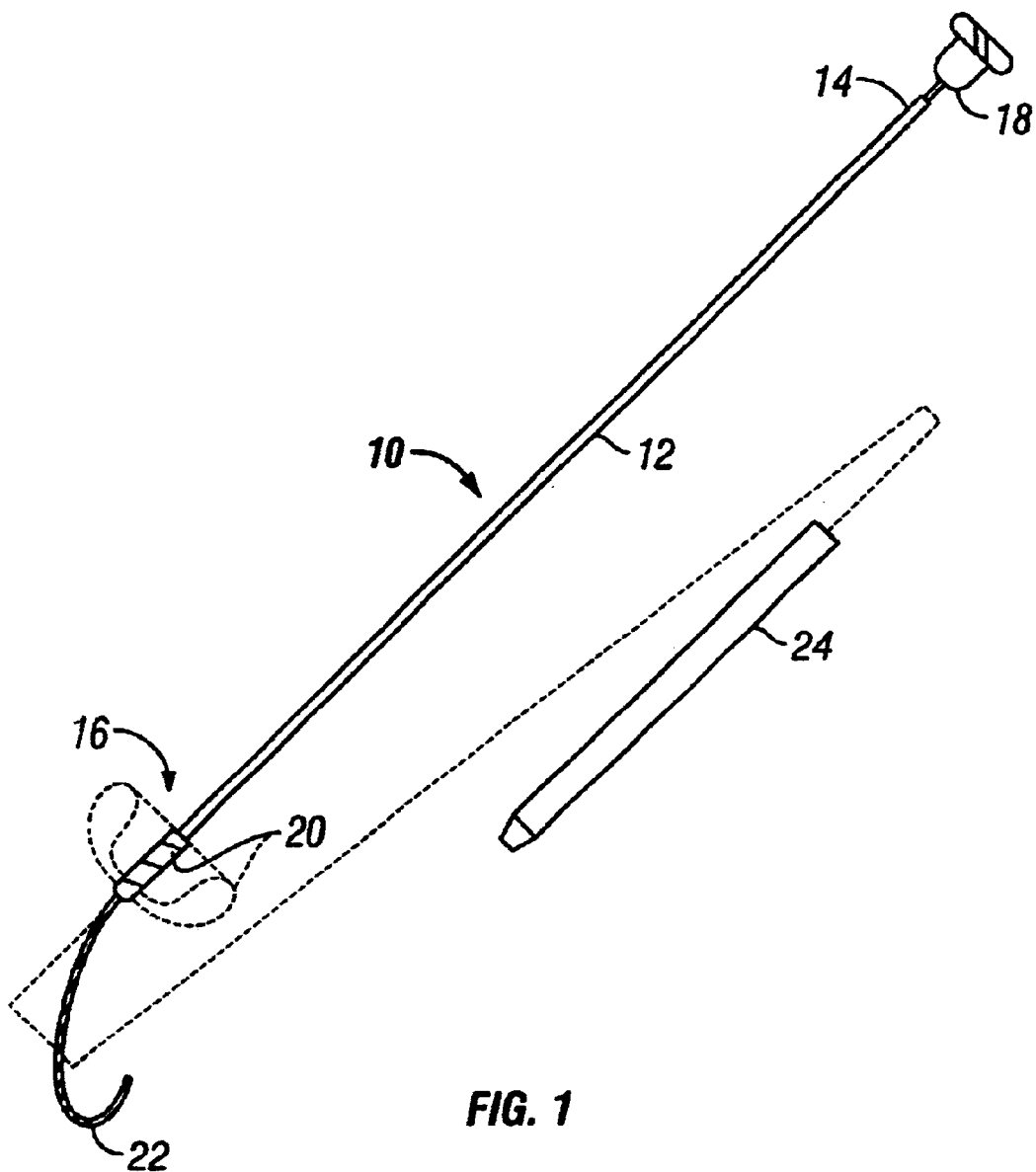
FIG. 1 illustrates a first embodiment of isolation apparatus constructed in accordance with the principles of the present invention.
Figure 2:
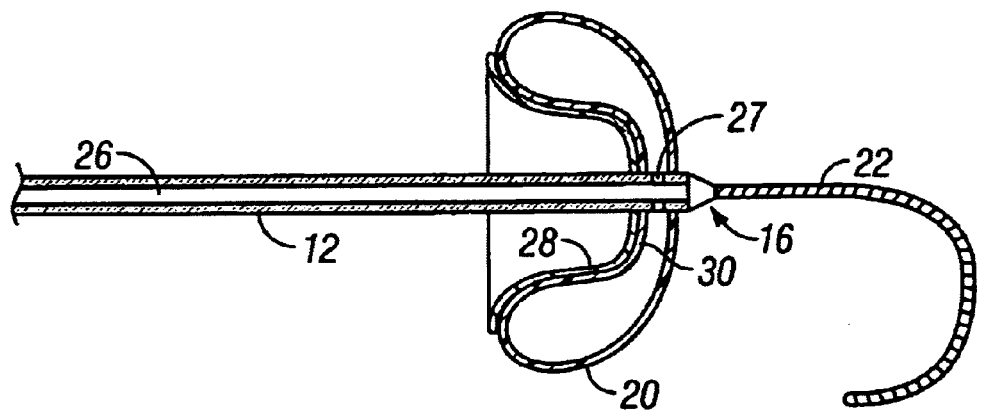
FIG. 2 is a detailed view of the distal end of the apparatus of FIG. 1, shown in partial section.

A first exemplary inflatable barrier tool 10 constructed in accordance with the principles of the present invention is illustrated in FIGS. 1 and 2. The inflatable barrier tool 10 comprises a shaft 12 having a proximal end 14 and a distal end 16. The shaft 12 may be formed from a variety of low diameter, medically acceptable tubular materials, such as hypotube. The shaft will usually have a diameter in the range from 0.4 mm to 1.4 mm, and a length in the range from 10 cm to 30 cm. Tool 10 further comprises an inflation of hub 18 which is removably attached to the proximal end 14. An inflatable barrier 20 is attached to the distal end 16 and illustrated in its deflated condition in full line and inflated condition in broken line (in FIG. 1). A guidewire 22 is fixed to the distal end 16 of the shaft 12, and a separate removal sheath 24 is provided. The removal sheath 24 has a central lumen (not shown) which is dimensioned to receive the shaft 12 and balloon 20 in its deflated condition.

As best shown in FIG. 2, the inflation hub 18 connects to an inflation lumen 26 which extends through the shaft and terminates in inflation ports 27 at the distal end 16 of the shaft. In this way, external inflation with a suitable medium, such as saline, can be used to expand the barrier 20 from its deflated condition to its fully inflated condition. A needle penetration-resistant layer 28 is formed over a concave surface 30 of the inflatable barrier 20. Typically, the layer will be laminated to the barrier 20. In the illustrated embodiment, the main body of the inflatable barrier 20 may be an elastomeric balloon which is molded into the desired cup-shaped geometry. The needle penetration-resistant layer 28 is then secured to the concave surface by adhesives, heat welding, or the like. Use of the device of FIGS. 1 and 2 will be described in detail in connection with FIGS. 6A–6F below.

Figure 3:
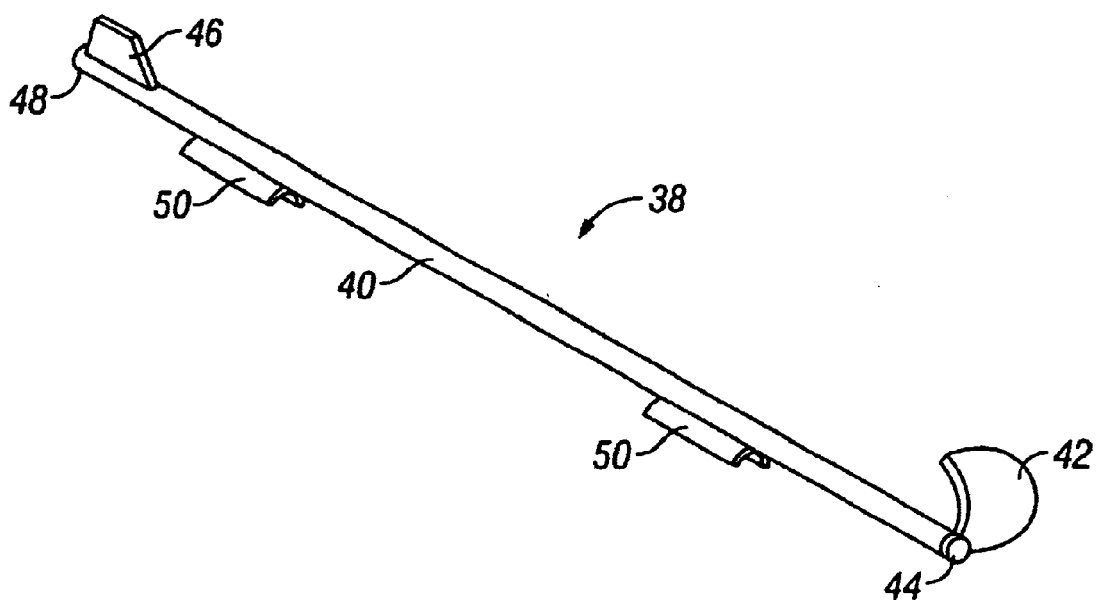
FIG. 3 illustrates a needle penetration shield tool which may be used in combination with the apparatus of FIG. 1.

As an alternative to including a needle penetration-resistant layer 28 on the concave surface 30 of the inflatable barrier 20, the apparatus of the present invention may include a separate needle shield tool 38, as shown in FIG. 3. The needle shield tool 38 comprises a shaft 40 (which may be solid core or hollow core) having an everted, pie-shaped shield element 42 at its distal end 44. A fin 46 or other marker is provided at the proximal end 48 to permit the user to visually align the position of the shield 42. Clamps 50 are provided at spaced-apart regions along the length of the shaft 40 in order to permit the tool 38 to be secured over the shaft 12 of tool 10. In this way, after the inflatable barrier 20 has been deployed at a desired anastomotic site, the tool 38 may be used to position shield 42 so that the needle penetration-resistant layer 28 may be eliminated. Elimination of the layer may be desirable to reduce the profile or diameter of the tool as well as to simplify manufacturing procedures. The shield 42 on tool 38 may then be rotated so that the shield protects the inflatable barrier 20 at the region where suturing or other potentially damaging procedures are being carried out. Alternative needle shield tool embodiments would allow for the tool to be loaded on to the shaft 12 of the inflatable barrier tool 10 via the central lumen within its shaft (not shown).

The inflatable barrier may take a variety of other forms as well. For example, as shown in FIG. 3A, an inflatable balloon 80 on shaft 82 has a recessible surface 84 which is pre-formed to have an annular channel 86 upon inflation. The precise geometry and dimensions of the channel 86 are chosen to accommodate the intended anastomotic procedure. Alternatively, as shown in FIG. 3B, a balloon 90 on shaft 92 has a recessible surface 94 which may be flat or even convex. In such cases, a needle barrier 96 or other rigid tool may be employed or temporarily create a recession 98 in the surface 94 of the balloon 90 by engaging the tool against the surface while the balloon is inflated. As described previously, the needle barrier 96 can be moved to both reform the working space and provide the desired protection against needle penetration.

Figure 4:
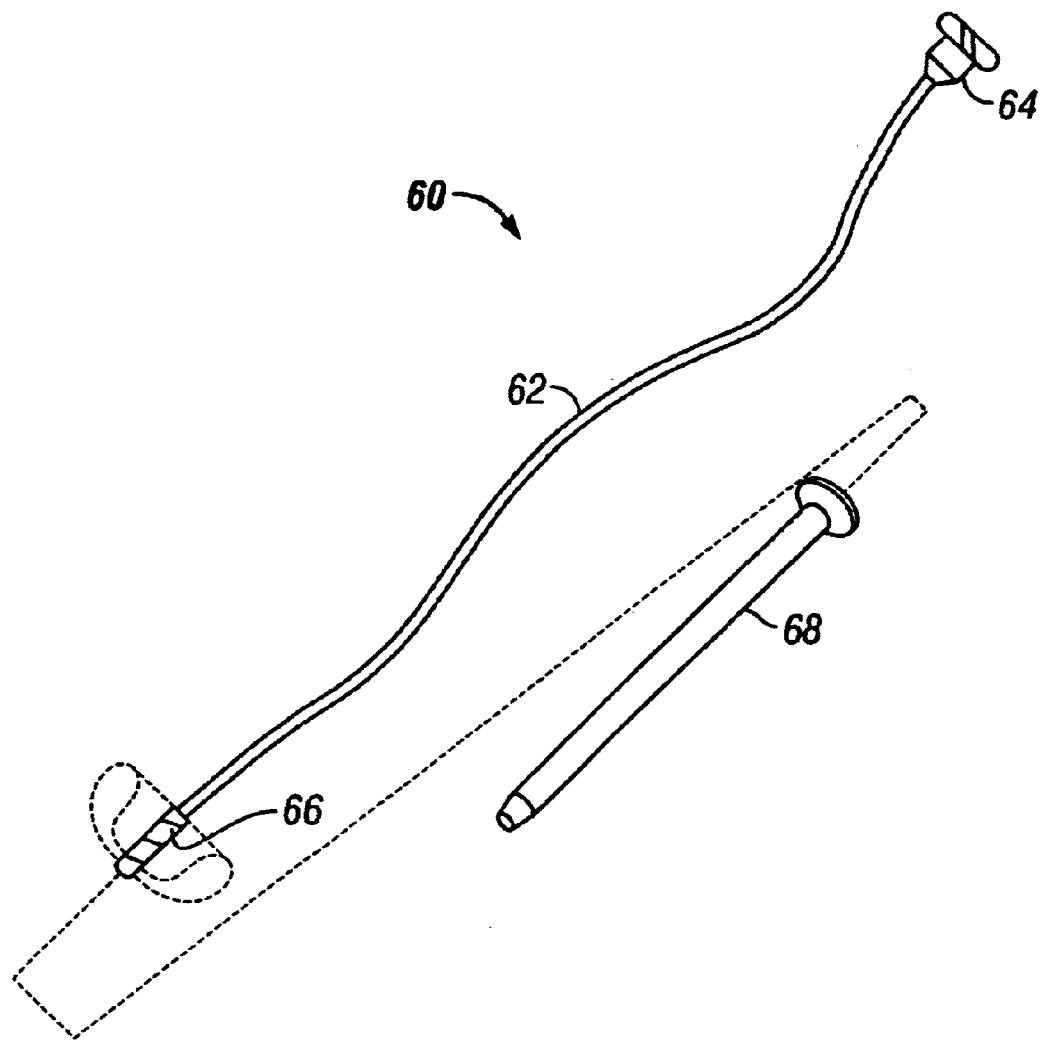
FIG. 4 illustrates a second embodiment of apparatus constructed in accordance with the principles of the present invention.

Referring now to FIG. 4, a second embodiment of the inflatable barrier tool 60 will be described. Tool 60 includes a shaft 62, hub 64, and inflatable barrier 66. The hub 64 and inflatable barrier 66 may be generally as described above in connection with inflatable barrier tool 10, but the shaft will differ. As illustrated, the shaft is formed from a non-rigid, axially extendable material. For example, shaft 62 may be formed from a tube of a rubbery or stretchable polymer, such as silicone rubber, latex, or the like. In this way, after the balloon 66 is deployed against the inner wall of a blood vessel, the force supplied against the blood vessel wall by the balloon may be modulated by stretching of the shaft as the shaft is pulled outwardly by the treating physician. In order to facilitate introduction of tool 60 having the non-rigid shaft 62, an introducer sheath 68 may be provided. The tool 60 is initially placed in the sheath 68, and the sheath 68 used to position the tool through a penetration in the blood vessel wall. The sheath may then be withdrawn over the shaft 62 of tool 60, and the inflation hub 64 then reconnected.

Figure 5:
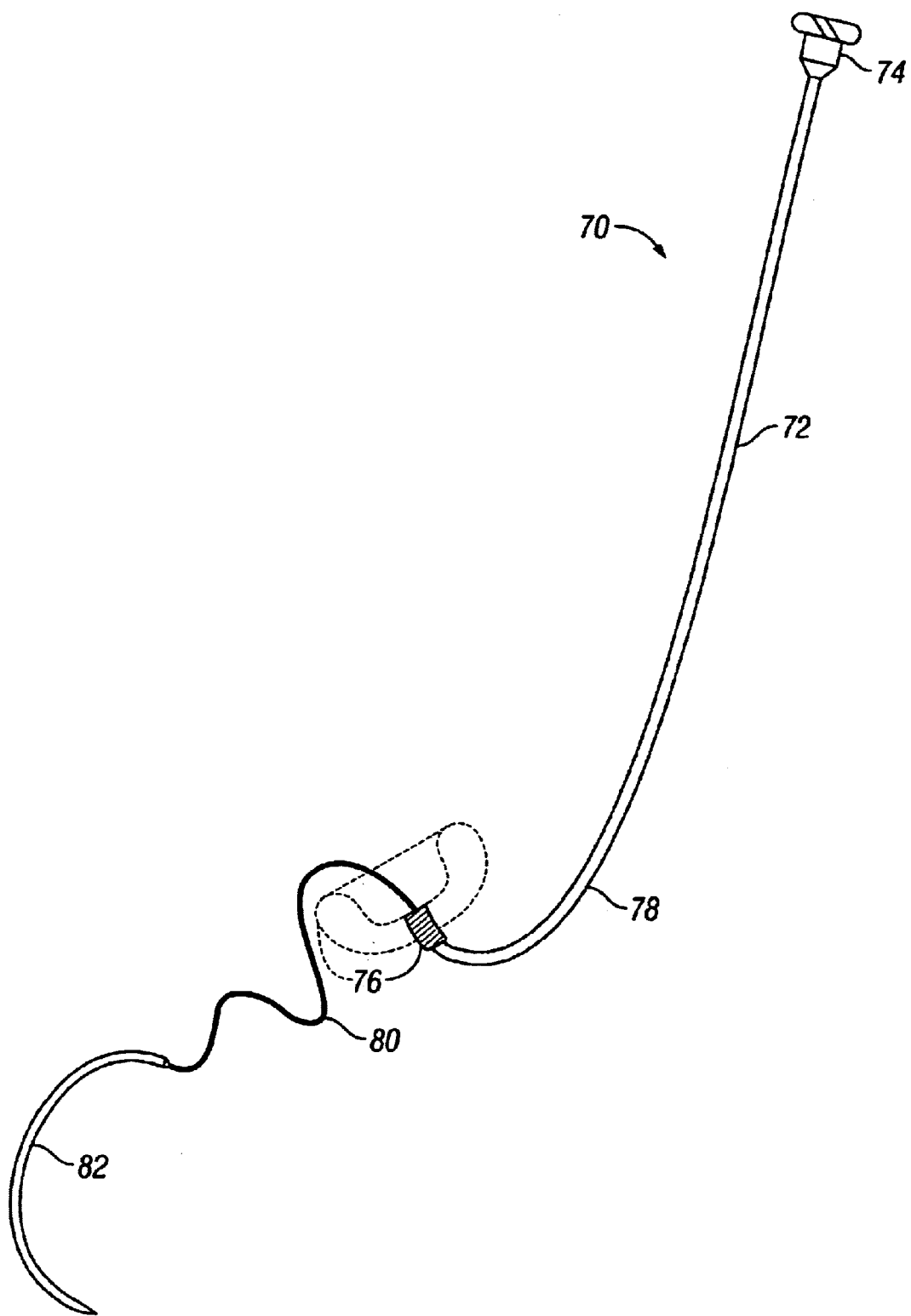
FIG. 5 illustrates a third embodiment of apparatus constructed in accordance with the principles of the present invention.

Referring now to FIG. 5, a third embodiment 70 of the inflatable barrier tool of the present invention will be described. Again, the tool 70 comprises a shaft 72, an inflation hub 74, and an inflatable barrier 76. The hub 74 and inflatable barrier 76 may generally be as described above, but the shaft will differ. The shaft 72 will generally be rigid, for example being formed from hypotube, but will have a curved distal region 78 which will facilitate proper positioning of the inflatable barrier 76 in certain protocols of the present invention, as described below in connection with FIGS. 7A–7F. The tool 70 further includes a tether 80, which may be suture, a single filament, or other medically acceptable wire, multi-filament bundle, or the like, and a curved needle 82.

Figure 6A:
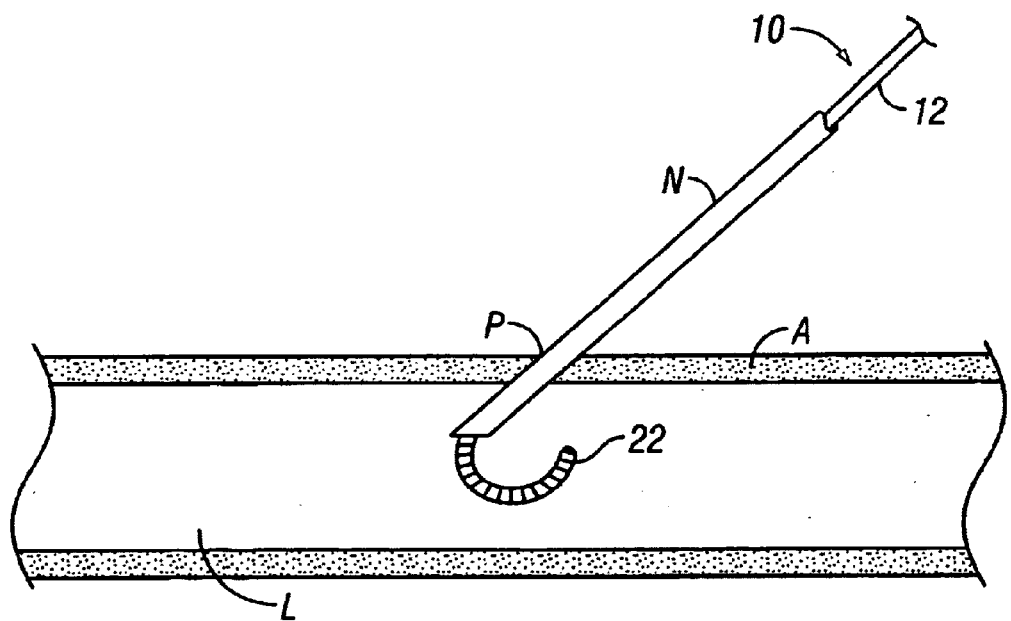
FIGS. 6A–6H illustrate use of the apparatus of FIG. 1 in performing methods according to the present invention.
Figure 6B:
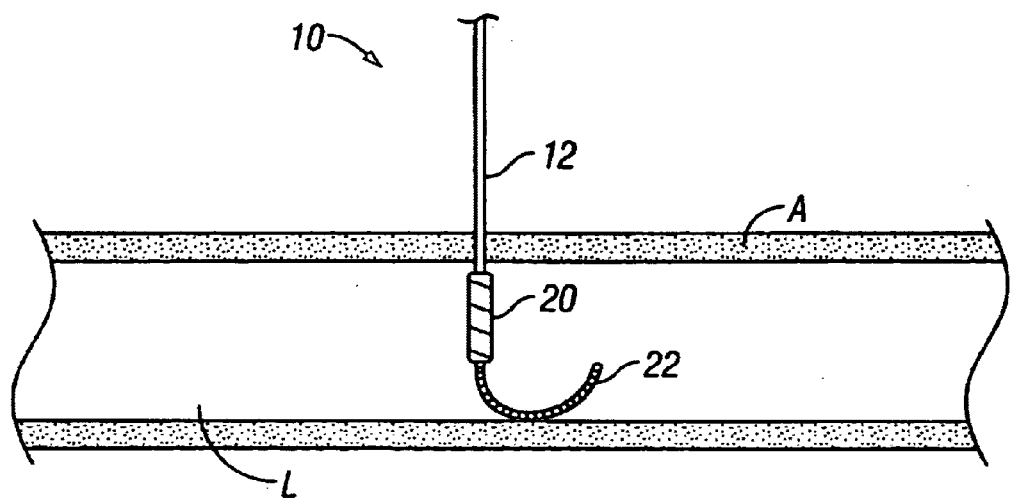
Figure 6C:
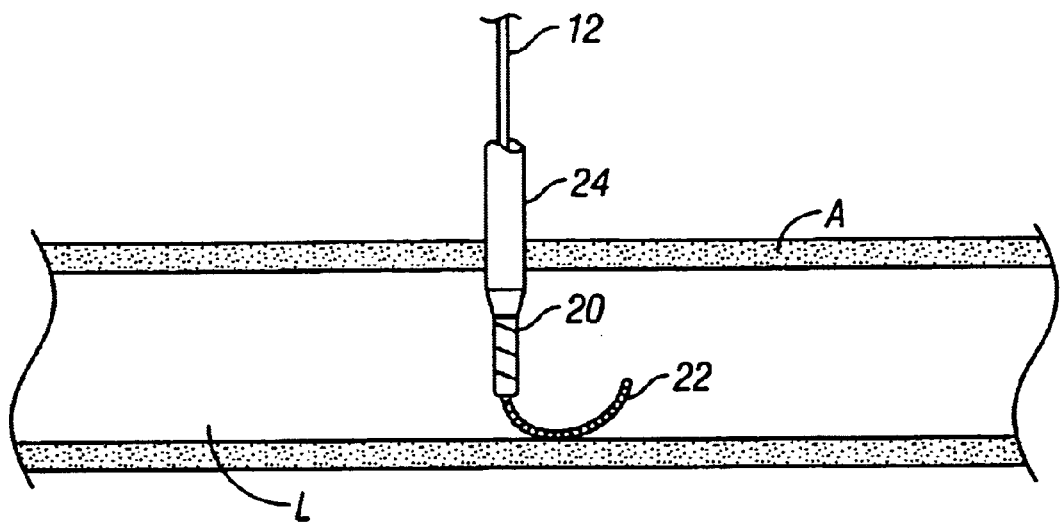
Figure 6D:
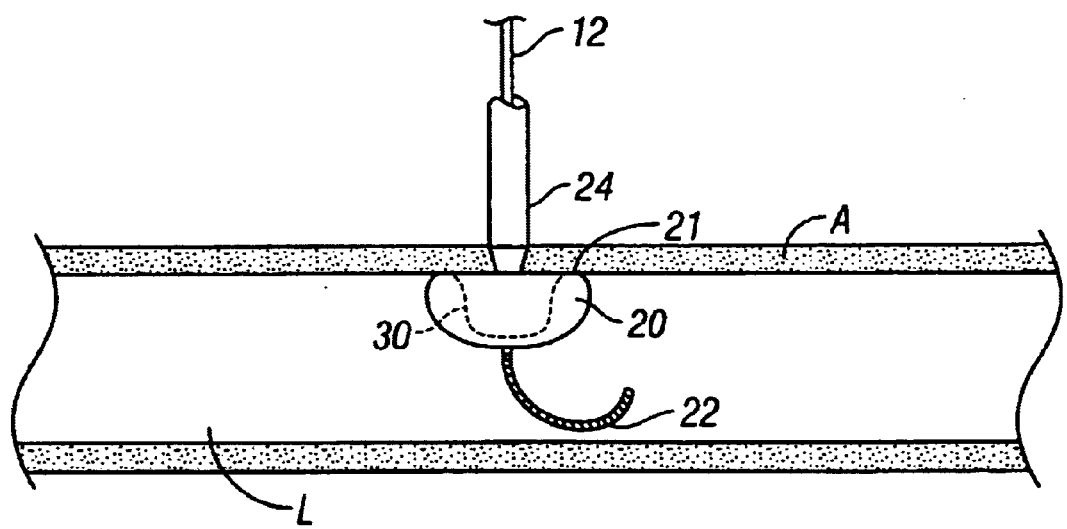

Referring now to FIGS. 6A–6H, use of the inflatable barrier tool 10 for forming an anastomotic attachment of a graft vessel GV (FIGS. 6G and 6H) to an aorta A will be described. Shaft 12 of the tool 10 will be introduced through a needle N which forms a penetration P in the wall of the aorta using a conventional Seldinger technique. The needle N is then withdrawn from over the shaft (from which the hub 18 has been removed), as shown in FIG. 6B and optionally the removal sheath 24 introduced over the shaft 12, as shown in FIG. 6C. The inflation hub 18 is then replaced (not shown) and the inflatable barrier 20 fully inflated, as shown in FIG. 6D. During this time, the fixed guidewire 22 helps assure that the tool 10 is properly placed within the lumen L of the aorta A.

Once deployed, the inflatable barrier 20 creates a working space defined by the concave surface 30, as shown in broken line in FIG. 6D. Isolation of the working space from blood which remains flowing through the aorta is assured by constantly pulling back on the shaft 12 in order to maintain a good seal between the periphery 21 of the inflatable barrier 20 and the inner wall of the aorta. The use of an elastomeric balloon as the inflatable barrier is particularly preferred in this regard since it will conform to the inner wall of the aorta with minimum trauma and with very good sealing.

Figure 6E:
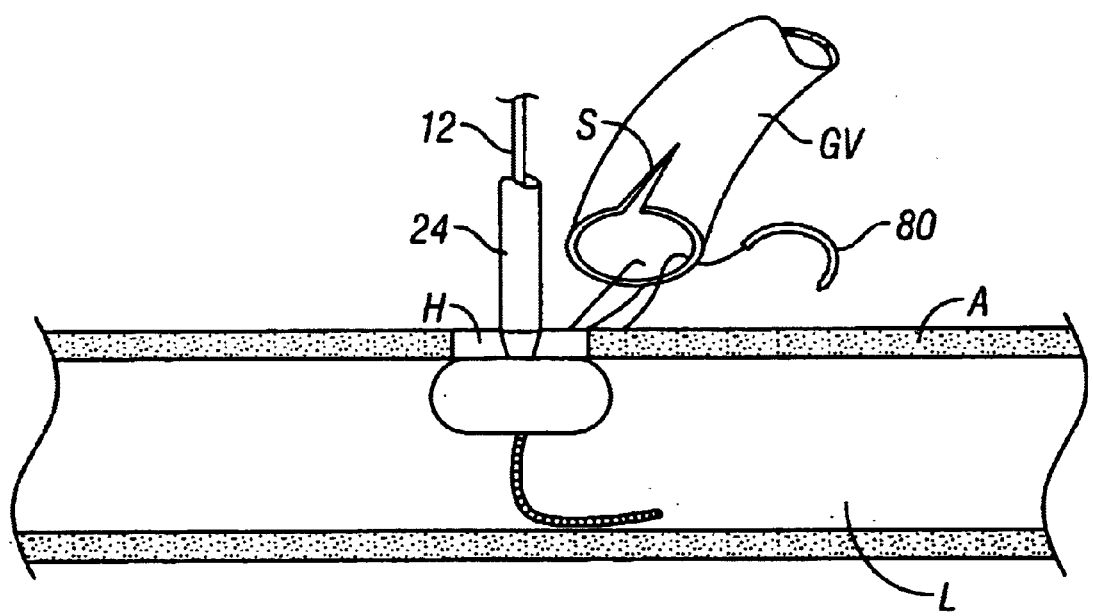
Figure 6F:
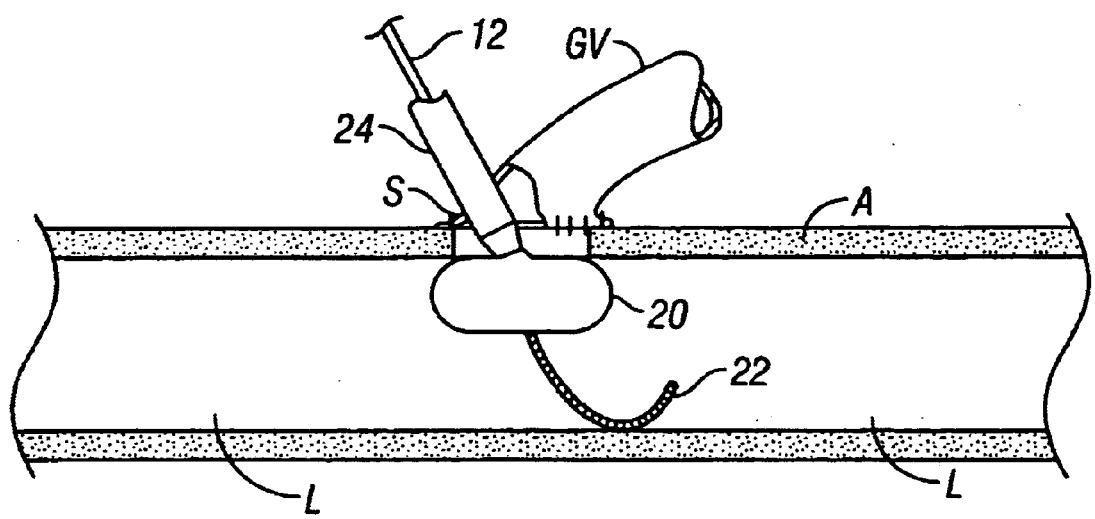
Figure 6G:
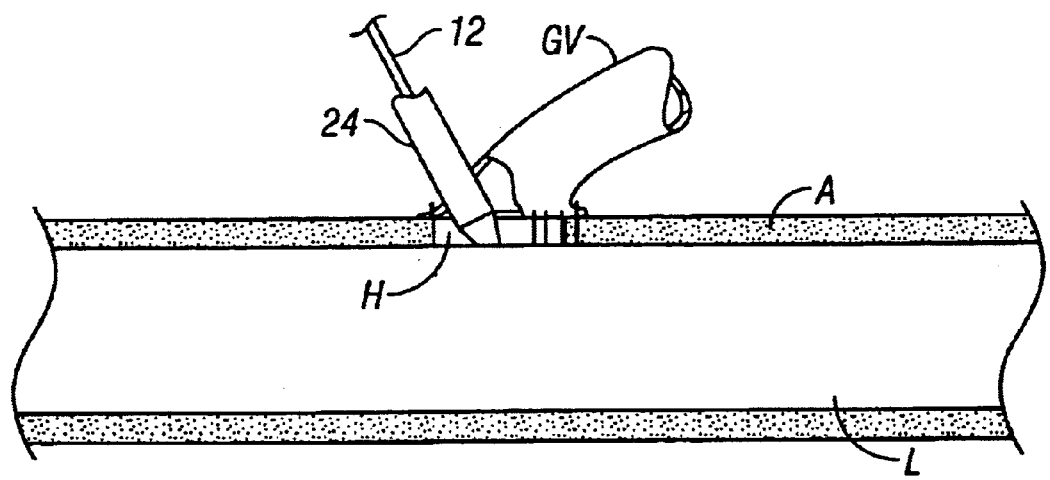
Figure 6H:
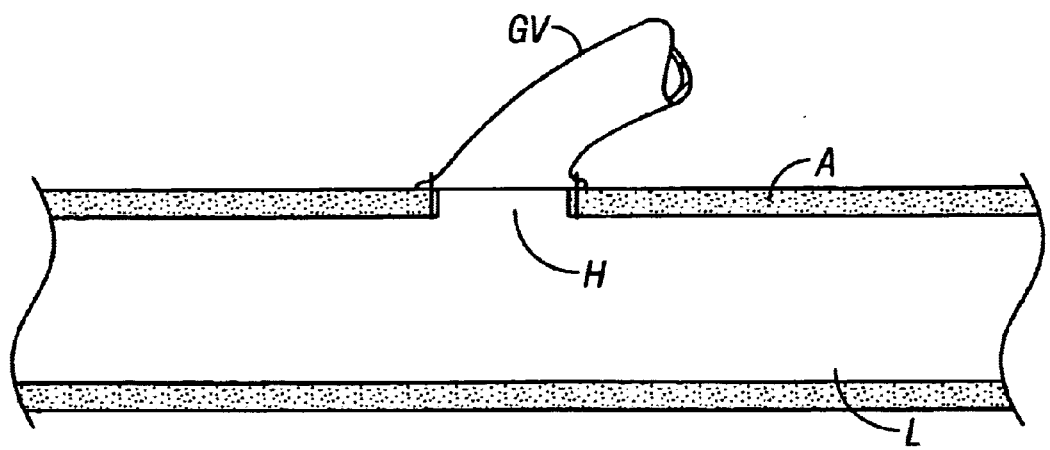

An anastomotic hole is next formed in the wall of the aorta A, as shown in FIG. 6E. The anastomotic hole may be produced by a conventional anastomotic hole punch. Optionally, the punch may be modified to have a channel or groove to accommodate presence of the tool shaft 12 and optionally removal sheath 24. After the hole is formed, the graft vessel GV will be brought in, and will optionally have a small split S to accommodate the tool shaft 12 and optionally removal sheath 24 as the anastomosis is formed. The anastomosis will be formed typically using suture, e.g., in a continuous suturing action using a conventional suturing needle 80 after the anastomosis is partially formed, as shown in FIG. 6F, the removal sheath 24 and tool shaft 12 will stand outwardly through the split S to permit withdrawal thereof. The inflatable barrier 20 will remain inflated to provide isolation until the anastomotic attachment is largely complete. At that point, the barrier 20 will be deflated and withdrawn back into the removal sheath 24, as shown in FIG. 6G. The removal sheath-inflatable barrier tool assembly is then withdrawn as the suture is tightened completing the anastomoses. Alternatively the removal sheath may then be withdrawn outwardly through the split S in the graft vessel GV. The anastomosis may then be completed and the split sutured in order to complete the anastomotic attachment, as shown in FIG. 6H.

Optionally, use of a tool having an elastic or resilient shaft, as shown in FIG. 4, permits control of the pull force on the vessel wall. In particular, the elasticity in the shaft reduces the risk of over tensioning the shaft and injuring the vessel wall. Such elastic shafts are also beneficial when the tool is to be connected to a sternal retractor or other mechanical support.

Figure 7A:
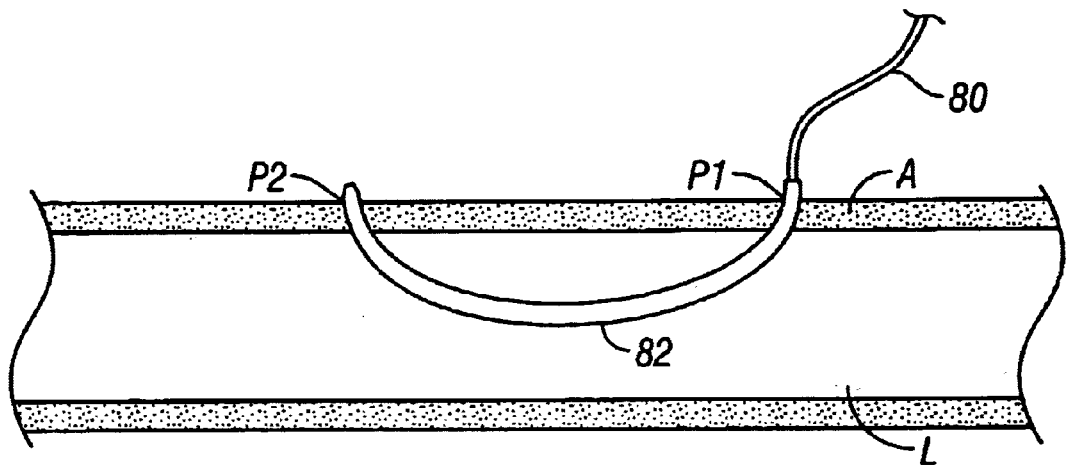
FIGS. 7A–7F illustrate use of the apparatus of FIG. 5 for performing methods in accordance with the principles of the present invention.
Figure 7B:
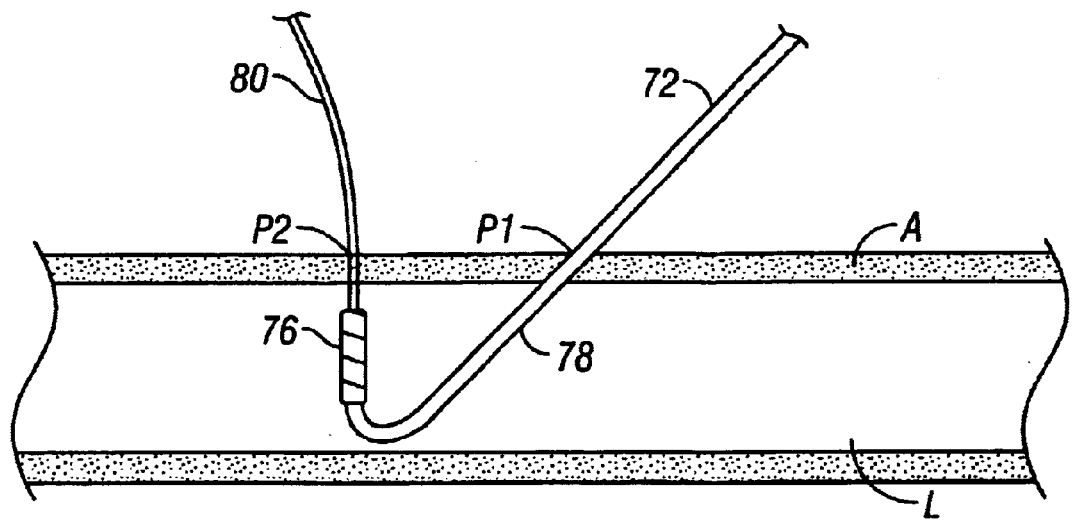
Figure 7C:
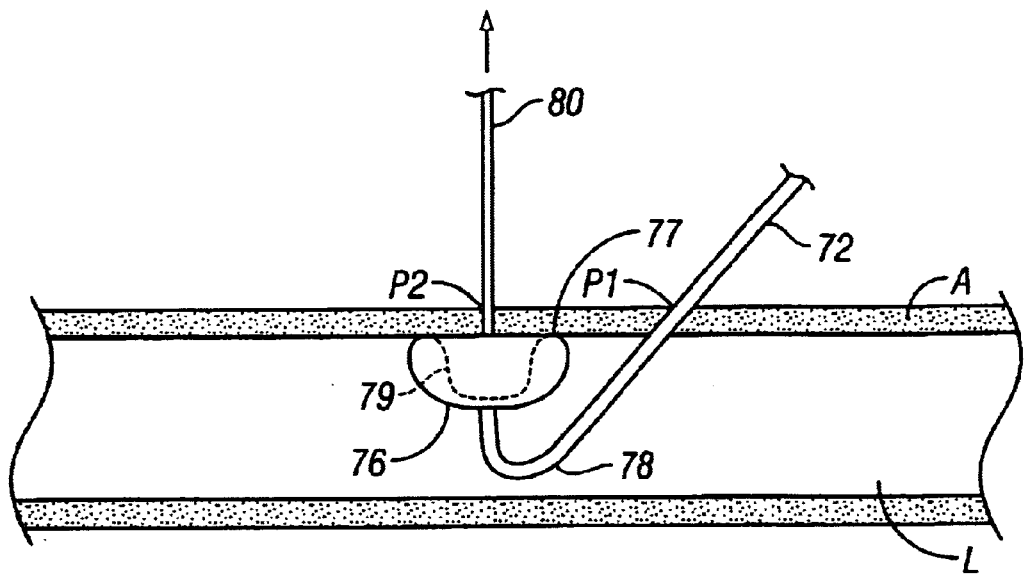

Referring now to FIGS. 7A–7F, use of the inflatable barrier tool 70 for performing an anastomotic attachment of a graft vessel GV in an aorta through a pair of spaced-apart penetrations in the aorta wall will be described. Initially, a curved needle 82 is first passed inwardly through the wall of the aorta A to form a first penetration $P_1$ and then outwardly to form a second penetration $P_2$. The first and second penetrations will be spaced-apart by distance usually in the range from 0.5 cm to 5 cm. The needle 82 is attached to tether 80, and the needle can thus be used to draw the tether through the first penetration $P_1$ and the second penetration $P_2$ so that the inflatable barrier 76 at the distal end of shaft 72 is brought up against the inner wall of the aorta at the second penetration $P_2$. The curved section 78 of the shaft 72 permits proper orientation of the inflatable barrier 76 so that, when inflated, it will lie with its sealing periphery 77 engaged against the inner wall of the aorta A, as shown in FIG. 7C. In this way, the inflatable barrier 76 may be urged against the inner wall of the aorta A by combination of both tension applied to the tether 80 and pushing applied by the shaft 72. In addition, the shaft 72 provides the necessary inflation lumen for the inflatable barrier 76 and will permit withdrawal of the inflatable barrier at the end of the procedure, as described below.

Figure 7D:
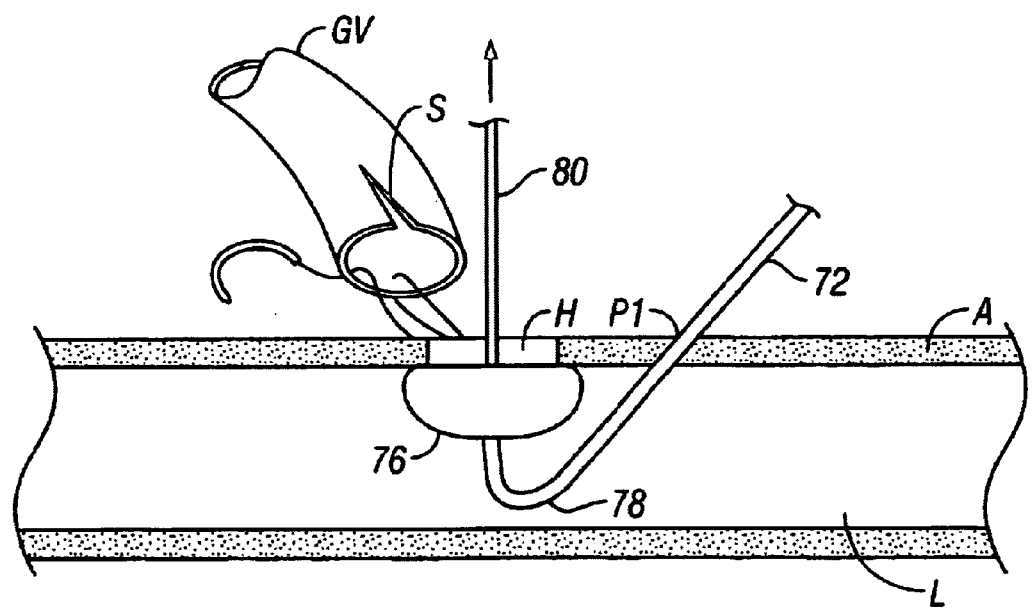

After the inflatable barrier 76 is inflated, the concave surface 79 thereof forms the working space in a manner analogous to that provided by the inflatable barrier 20 of the first tool 10. An anastomotic hole H may then be formed using a conventional or modified punch, as shown in FIG. 7D, and the graft vessel GV sutured to the hole H using conventional needle and suture, as shown in FIG. 7D. Optionally, a slit S may be provided in the graft vessel GV, although this will not always be necessary.

Figure 7E:
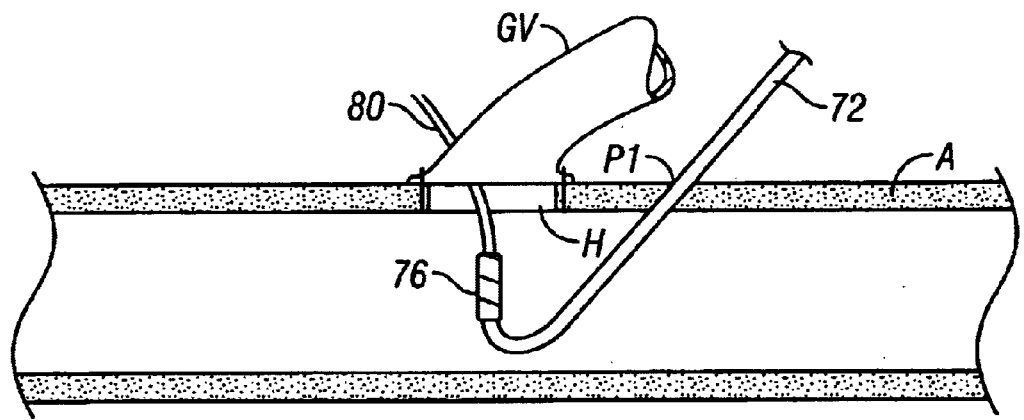
Figure 7F:
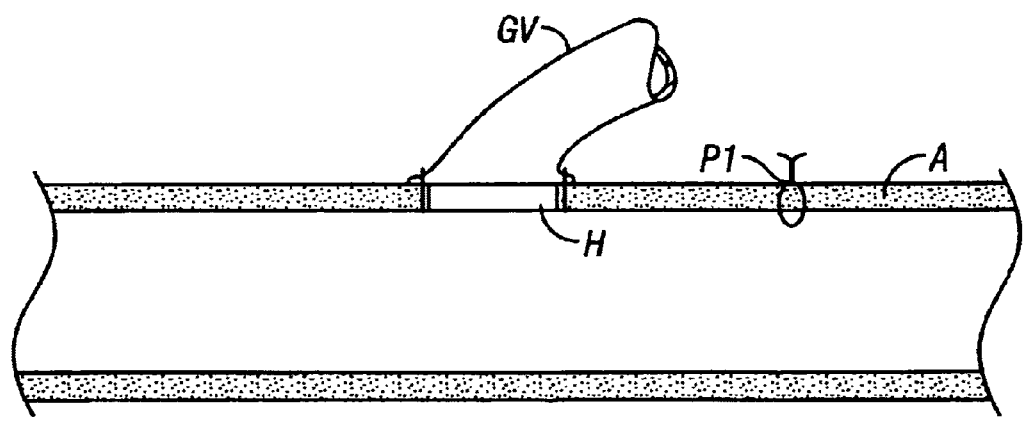

After the anastomotic attachment is essentially complete, as shown in FIG. 7E, the inflatable barrier 76 may be deflated, leaving only the tether 80 passing through the anastomosed interface between the graft vessel GV and aorta A. Usually, the needle will be clipped from the tether, and the tether may be simply pulled backward through the hole H and then outwardly through the first penetration as the shaft 72 is withdrawn. At the end of the procedure, the graft vessel GV is completely anastomosed to the aorta A and the penetration $P_1$ is separately sutured, as shown in FIG. 7F.

Figure 8:
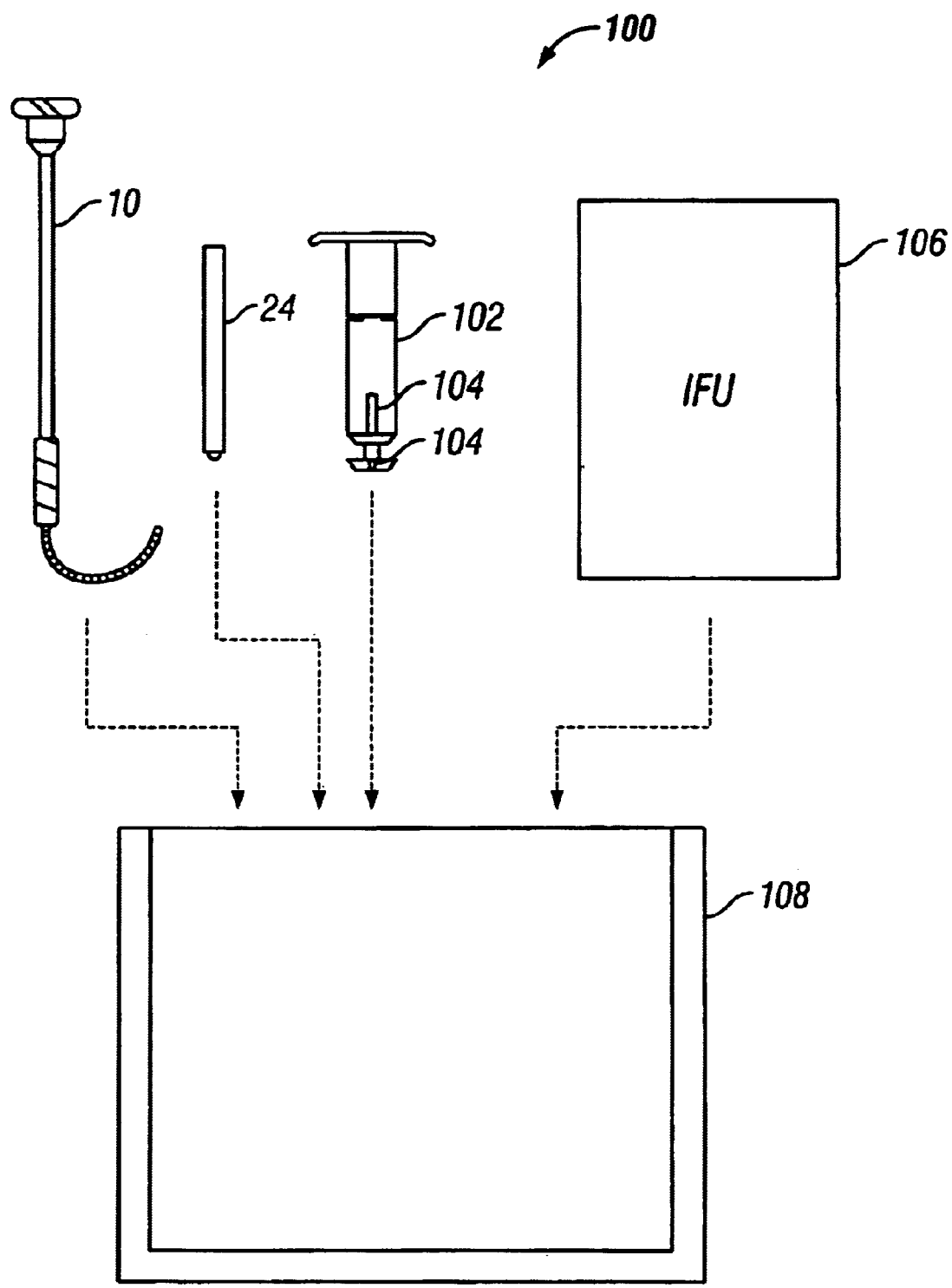
FIG. 8 illustrates a kit constructed in accordance with the principles of the present invention.

Referring now to FIG. 8, kits 100 according to the present invention may comprise any one or more of the system components, such as tool 10 (or tools 60 or 70), removal sheath 24 (or introducer sheath 68), and/or a hole punch 102, needle (not shown), syringe (not shown), or the like. A hole punch 102 is shown as being modified with a channel 104 formed in its side to accommodate presence of the catheter 10 during the anastomosing procedures. The kits 100 will also include instructions for use IFU which may be printed on a separate instruction sheet 106 and/or which may be printed in whole or in a part on product packaging 108. The packaging 108 accommodates any one or more of the system components, preferably in a sterile manner, and may comprise any conventional medical device package, such as a box, tray, tube, pouch, or the like. Instructions for use IFU may set forth any of the methods described herein and employing the system components which are packaged therewith.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for forming an anastomotic site in a body lumen having a wall with an outer surface, an inner surface, and an interior lumen, said method comprising:

positioning an inflatable barrier having a recessible surface within the body lumen;

inflating the barrier to form a working space;

tensioning the inflated barrier to seal against the inner surface of the wall while a portion of the body lumen remains unblocked by the inflated barrier;

cutting a hole through the wall into the working space to create the anastomotic site; and introducing a needle shield through the hole to protect the inflatable barrier during subsequent anastomotic suturing.

2. A method as in claim 1, wherein inflating the barrier creates a recessed surface disposed toward the inner surface of the body lumen and wherein positioning comprises introducing the barrier in a deflated condition through a penetration in the wall into the interior lumen and drawing the recessed surface of the barrier back against the inner surface of the wall to tension the barrier against the inner surface of the body lumen and locate the working space over the penetration.

3. A method as in claim 2, wherein the inflatable barrier has an inflated geometry which defines the recessed surface.

4. A method as in claim 3, wherein the recessed surface defined by the inflated geometry is concave or an annular groove.

5. A method as in claim 2, wherein positioning the inflatable barrier comprises introducing a catheter having the barrier at a distal end thereof through a needle.

6. A method as in claim 5, wherein introducing further comprises exchange of the needle for a removal sheath.

7. A method as in claim 6, wherein cutting the hole comprises introducing a cutting die over or adjacent to the catheter, and wherein the cutting die opens a hole into the working space.

8. A method as in claim 7, wherein the cutting die is advanced adjacent to the catheter, and wherein the cutting die includes a channel to align the die with the catheter as the die is advanced.

9. A method as in claim 6, 7, or 8, further comprising attaching a distal end of a graft vessel to the anastomotic site, wherein the removal sheath is disposed between the graft vessel and hole in the blood vessel wall.

10. A method as in claim 9, further comprising deflating the barrier and withdrawing the deflated barrier through or into the removal sheath prior to removing the removal sheath from between the graft vessel and the hole in the blood vessel wall.

11. A method as in claim 5, wherein the recessible surface of the barrier is drawn against the inner surface of the blood vessel wall by pulling on the catheter.

12. A method as in claim 11, wherein the catheter yields in response to axial tension so that the force applied by the recessible surface of the barrier against inner surface of the blood vessel wall is modulated.

13. A method as in claim 1, wherein the needle shield is engaged against the recessible surface to create the working space.

14. A method as in claim 1, wherein positioning the inflatable barrier comprises introducing the barrier in a deflated condition through a first penetration in the blood vessel wall into the lumen, advancing the barrier axially through the lumen away from the penetration, inflating the barrier, and engaging the recessible surface of the barrier against the inner surface of the blood vessel wall to locate the working space away from the first penetration.

15. A method as in claim 14, wherein tensioning the inflated barrier comprises forming a second penetration at the desired location of the working space, passing a tether attached to the barrier through the second penetration, and pulling on the tether to hold the recessible surface of the barrier against the inner surface of the blood vessel wall.

16. A method as in claim 14 or 15, wherein introducing the inflatable barrier comprises advancing the barrier with a shaft passing through the first penetration, wherein an end of the shaft attached to the barrier is curved to facilitate locating the recessible surface of the barrier against the inner wall of the blood vessel.

17. A method as in claim 16, further comprising attaching a distal end of a graft vessel to the anastomotic site, wherein the tether is disposed between the graft vessel and the hole in the blood vessel wall.

18. A method as in claim 17, further comprising deflating the barrier and withdrawing the catheter, deflated balloon, and tether through the second penetration.

19. A method as in claim 18, wherein the second penetration is closed after withdrawing the catheter barrier, and tether.

20. A method as in claim 15, wherein cutting the hole comprises introducing a cutting die over or adjacent to the tether.

21. A method as in claim 20, wherein the cutting die is advanced adjacent to the tether and wherein the cutting die includes a channel to align the die with the tether as the die is advanced.

22. A method as in claim 1, further comprising suturing a distal end of a graft vessel to the anastomotic site in the blood vessel with a needle.

* * * * *